(12) United States Patent
Barack

(10) Patent No.: US 8,579,874 B1
(45) Date of Patent: Nov. 12, 2013

(54) BREAST INTERFACE ASSEMBLY FOR BREAST PUMP

(75) Inventor: Doron Barack, Raanana (IL)

(73) Assignee: Portable Technologies Ltd., Raanana (IL)

( * ) Notice: Subject to any disclaimer, the term of this patent is extended or adjusted under 35 U.S.C. 154(b) by 0 days.

(21) Appl. No.: 13/596,071

(22) Filed: Aug. 28, 2012

(51) Int. Cl.
*A61F 5/44* (2006.01)

(52) U.S. Cl.
USPC ................ 604/346; 220/914; 604/74

(58) Field of Classification Search
CPC ........................................................ A61M 1/06
USPC ............... 220/914; 604/74–76, 313, 315, 346
See application file for complete search history.

(56) References Cited

U.S. PATENT DOCUMENTS

| | | | | |
|---|---|---|---|---|
| 2004/0024352 | A1* | 2/2004 | Renz et al. | 604/74 |
| 2008/0171970 | A1* | 7/2008 | Luzbetak et al. | 604/74 |
| 2009/0030368 | A1* | 1/2009 | Silver | 604/74 |
| 2011/0251552 | A1* | 10/2011 | Brittner | 604/74 |
| 2012/0035536 | A1* | 2/2012 | Gottenbos et al. | 604/74 |
| 2012/0071820 | A1* | 3/2012 | Luzbetak et al. | 604/74 |
| 2012/0101432 | A1* | 4/2012 | Silver | 604/74 |
| 2013/0123688 | A1* | 5/2013 | Bosman et al. | 604/74 |

* cited by examiner

*Primary Examiner* — Nicholas Lucchesi
*Assistant Examiner* — Gerald Landry, II
(74) *Attorney, Agent, or Firm* — Mark M. Friedman

(57) ABSTRACT

A breast interface assembly for connecting a breast pump to a nipple of a breast, includes a connector and a reversible element which has two terminal portions of differing internal diameters. The breast interface assembly is configured to be assembled in a first state, in which a first terminal portion of the reversible element connects with the connector, and the breast interface assembly presents a breast contact surface defining a nipple aperture of a first diameter. The breast interface assembly is further configured to be assembled in a second state in which a second terminal portion of the reversible element connects with the connector and the breast interface assembly presents a breast contact surface defining a nipple aperture of a second diameter. In at least one of the first and second states, the reversible element provides at least part of the breast contact surface.

10 Claims, 4 Drawing Sheets

BREAST INTERFACE ASSEMBLY FOR BREAST PUMP

FIELD AND BACKGROUND OF THE INVENTION

The present invention relates generally to breast pumps, and more particularly to a breast interface assembly for connecting a breast pump to a nipple of a breast.

Breast milk pumps are well known in the art. Breast milk pumps generally have a breast shield (also known as a suction hood), a connector, and a suction/vacuum device. The breast shield has a generally—conical shape and a central stem, much like a funnel, and is usually made of a transparent plastic, to allow the user to ensure proper fitting. The conical portion fits over a portion of the breast, while the nipple fits tightly into the central stem. Milk is extracted by rapidly changing the pressure within the central region in a cyclic manner, drawing the nipple towards the connector each time the pressure is reduced in a process known medically as "the milk ejection response". The pressure may be altered manually, by pulling or squeezing a handle, or electrically, by connecting up to a vacuum pump and intermittently alternating the pressure; ideally, at a rate of between thirty and sixty cycles per minute. Expressed breast milk (EBM) drains from the breast shield into the milk port, flowing down a length of tubing in most cases.

Various attempts have been made to improve upon the first breast pump of 1854 and subsequent improvements to it. In an attempt to offer a product that fits every nursing mother perfectly, breast milk pumps come with a variety of sizes of breast shields. Variations in breast shield size tend to be in the size of the tubular end, which typically comes in the range of between 24 mm and 36 mm, but also includes a variety of sizes of the conical end. For example, U.S. Pat. No. 6,723,066 to Larsson et al. and titled "Breastpump with Universal Hood Base and Interchangeable Suction Hoods" describes a common suction hood base that can be used with a number of different sized shields. U.S. Pat. No. 4,857,051 to Larsson and titled "Breastpump" describes several ideas including an adjustment piece for decreasing the cross-sectional area of a funnel-shaped hood member. The hood member is another name for a breast shield. In this patent, a smaller-sized funnel is fitted inside a regular funnel-shaped breast shield to improve the fitting for smaller breasts.

Commercially, a breast pump is sold with a selection of breast shields that have similar sized conical ends, while the tubular end comes in a variety of bore sizes that vary by 1 mm. It would be highly advantageous and economical to simplify fitting the breast shield over a mother's breast by altering the tubular end of the breast shield.

SUMMARY OF THE INVENTION

According to the present invention there is provided a breast interface assembly for connecting a breast pump to a nipple of a breast, including a milk inlet port and a reversible element which has two terminal portions of differing internal diameters. The breast interface assembly is configured to be assembled in a first state, in which a first terminal portion of the reversible element connects with the milk inlet port, and the breast interface assembly presents a breast contact surface defining a nipple aperture of a first diameter. The breast interface assembly is further configured to be assembled in a second state in which a second terminal portion of the reversible element connects with the milk inlet port and the breast interface assembly presents a breast contact surface defining a nipple aperture of a second diameter. In at least one of the first and second states, the reversible element provides at least part of the breast contact surface.

According to further features in preferred embodiments of the invention described below, the breast interface assembly further includes a breast shield including a flange portion. The breast shield is configured to connect with the second terminal portion of the reversible element in the first state and with the first terminal portion of the reversible element in the second state. The breast shield provides at least part of the breast contact surface in each of the first and second states.

According to still further features in the described preferred embodiments, the breast shield further includes a tubular portion. The reversible element is configured such that the second terminal portion connects internally to the tubular portion such that an internal diameter of the second terminal portion defines the nipple aperture of the first diameter, and the first terminal portion connects externally to the tubular portion such that the tubular portion defines the nipple aperture of the second diameter.

According to another embodiment, the breast interface assembly further includes a second reversible element which has two terminal portions with third and fourth internal diameters that differ from the first and second nipple aperture diameters. The second reversible element is configured for interconnecting between the milk inlet port and the breast shield in each of two configurations with the terminal portions connecting internally to the tubular portion such that internal diameters of the terminal portions define nipple apertures with the third and fourth diameters.

According to yet another embodiment, the breast shield further includes a tubular portion. The reversible element is configured such that both the first and second terminal portions connect internally to the tubular portion such that internal diameters of the terminal portions define the nipple aperture of the first and second diameters.

Optionally, the reversible element has at least one abutment feature deployed to prevent over-insertion of the reversible element into the tubular portion of the breast shield.

According to further features in preferred embodiments of the invention, the edges of the reversible element that provide the breast contact surface are rounded so as to merge with a skin contact surface of the flange portion.

According to yet another embodiment the reversible element includes a flexible section to accommodate flexing of the reversible element between the first and second terminal portions.

According to another embodiment still, each of the first and second terminal portions of the reversible element is configured for direct sealing contact with the nipple without requiring an outwardly extending flange.

BRIEF DESCRIPTION OF THE DRAWINGS

Various embodiments are herein described, by way of example only, with reference to the accompanying drawings, wherein.

DESCRIPTION OF THE PREFERRED EMBODIMENTS

The present invention provides a breast interface assembly that addresses various shortcomings of the presently known configurations by providing one or more reversible components that may be fitted in two alternate configurations, offering two or more sizes of nipple aperture.

In a first configuration of assembly, a reversible element is connected at a first end to a nipple of a breast, in some cases with the aid of a breast shield, and, at a second end, to a connector. In a second configuration of assembly, at the first end, the reversible element is connected to the connector, and at the second end, to the nipple, again in some cases with the aid of the breast shield. The reversible element has terminal portions with differing internal diameters, such that the two configurations of the breast interface assembly define nipple apertures of two differing diameters. When assembled in the first state, a first nipple aperture is presented. When assembled in the second state, a second nipple aperture is presented.

The principles and operation of a breast shield according to the present invention may be better understood with reference to the drawings and the accompanying description.

Figure 1:
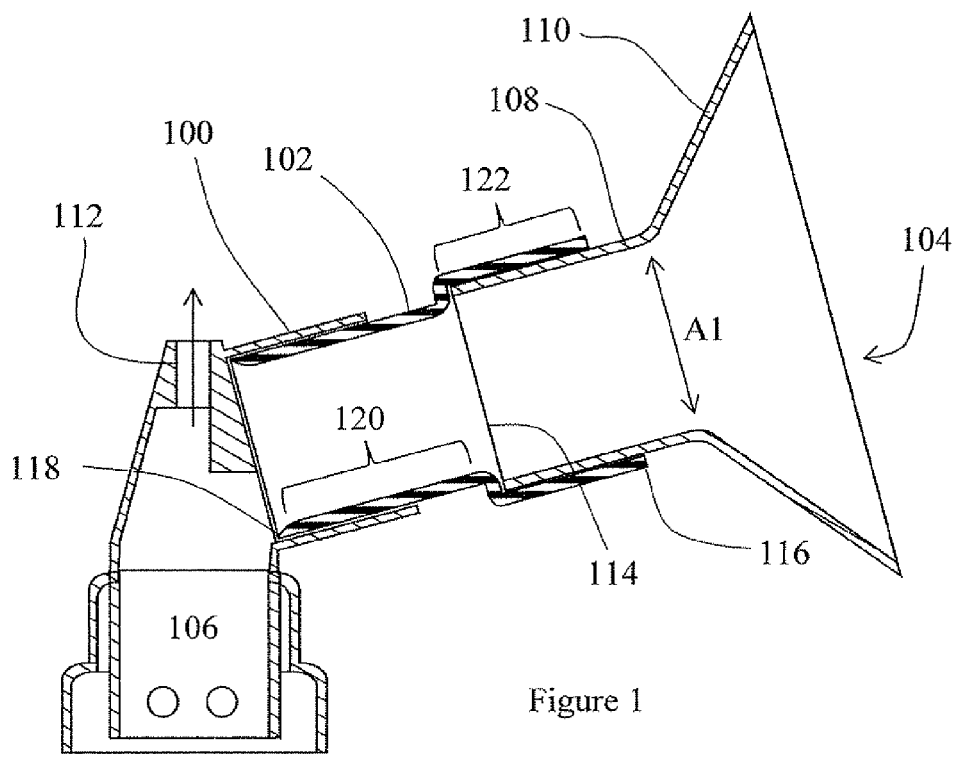
FIG. 1 is a cross-sectional view of a breast interface assembly including a dual-diameter reversible element, showing the assembly in a first state.

Referring now to the drawings, FIG. 1 is a cross-sectional view of a breast interface assembly including a dual-diameter reversible element, showing the element in a first state of assembly. In the first state, a reversible element 102 is connected at a first terminal portion to a breast shield 104 and, at a second terminal portion, to a connector 106. The breast shield 104 has a tubular portion 108 and a flange portion 110 which is typically generally conical and serves as the breast shield or "hood". In the example illustrated, the nipple aperture A1 is implemented as an aperture of the tubular portion 108. Connections between the elements are preferably by interference fit, also known as a press-fit seal, commonly used when engaging overlapping tubes. The tubular portion 108 (light shading) mates the first terminal portion 122 of the reversible element 102 (heavy shading) such that the reversible element 102 engages an external surface of the tubular portion 108.

The flange portion 110 is pressed against a breast of a nursing mother such that some of the breast is enclosed by the breast shield 104. A nipple is directed into the tubular portion 108 of the breast shield 104. A vacuum draws air out of a suction port 112 of the connector 106. The vacuum is preferably intermittent, but may also be continuous. The low pressure acts on the nipple within the tubular portion 108, expressing milk. The expressed milk flows down by gravity to be collected in a vessel (not shown).

Edge 114 of the tubular portion 108 of the breast shield 104 is pressed home against the inner surface of a narrowing portion of reversible element 102, to ensure no gaps or edges protrude into the inner cavity. Maintaining a smooth inner cavity is important for the comfort of the nursing mother and ensures milk does not lodge in a crevice. Outer edge 116 does not have to be tapered since outer edge 116 lies outside the inner cavity. Inner edge 118 is tapered since it lies inside the inner cavity, and, when the reversible element 102 is reversed, may touch the breast. In this context, the term "breast contact surface" is used to refer collectively to the sum total of the breast contact surface which may be made up of a number of constituent surfaces, such as an end of the reversible element together with the flange portion 110 of breast shield 104.

Connector 106 is typically the top or lid of a receptacle. The connector 106 may also be a cover for a suction chamber. In a preferred embodiment, a complete receptacle (not shown) is a non-flexible vessel, able to withstand the vacuum pressure. The complete receptacle includes a vessel, such as a bottle, or the like, for containing the milk, and a suction port 110 at the top, as far as possible from the flowing stream of milk. A suction device is attached to the suction port for use. Preferably, the suction port is shielded from milk that may inadvertently get drawn in by the vacuum. A milk inlet port 100 is defined to be the opening on the connector 106 to which the reversible element 102 is connected.

A nipple aperture is defined as follows: Reversible element 102 is configured such that a second terminal portion 120 connects internally to connector 106. In other words the internal surface of connector 106 mates with the external surface of the second terminal portion 120. At the other end of reversible element 102, a first terminal portion 122 connects externally to tubular portion 108. In other words, the external surface of the tubular portion 108 mates with the internal surface of the first terminal portion 122. In such a fashion, a nipple aperture A1 is defined.

Figure 2:
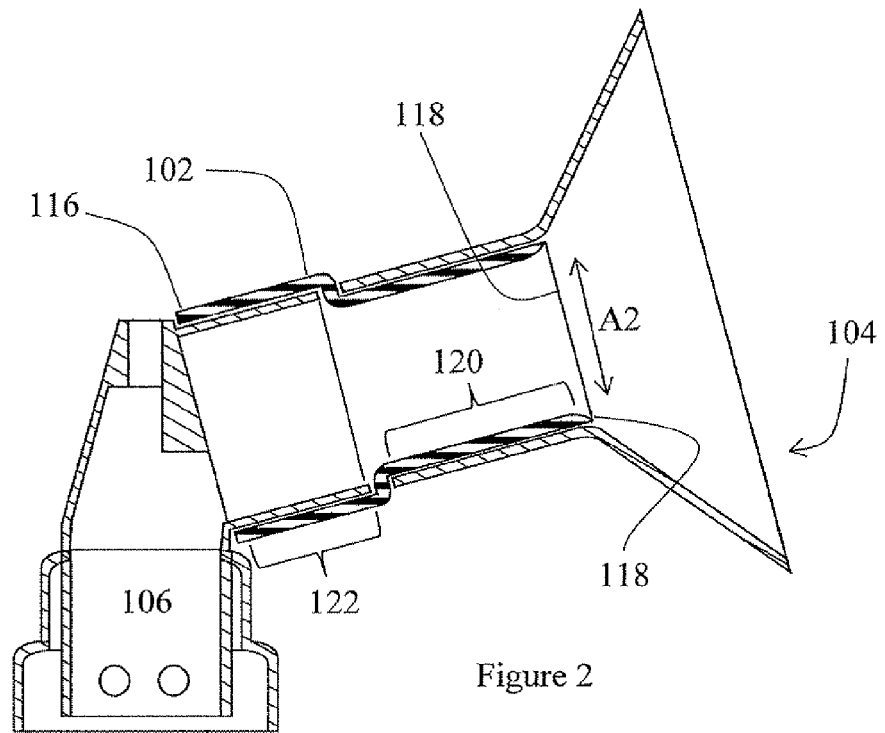
FIG. 2 is a cross-sectional view of the breast interface assembly of FIG. 1, showing the assembly in a second state.

FIG. 2 is a cross-sectional view of the breast interface assembly of FIG. 1, showing the reversible element in a second configuration. In the example illustrated, the nipple aperture A2 is implemented as an aperture of the reversible element 102. A second terminal portion 120 connects internally to tubular portion 108. In other words, the internal surface of tubular portion 108 mates with the external surface of second terminal portion 120. In so doing, a nipple aperture A2 is produced, such that A2 is smaller than A1. Edge 118 is tapered in order to form a continuous smooth surface with the flange portion 110 of the breast shield 104.

It will be noted that the portion of the reversible element defining the nipple aperture is referred to as the "terminal portion". This refers to a region close to an end of the reversible element, but neglecting any outwards rounding-off or tapering of the walls of the reversible element at its ends.

Figure 3:
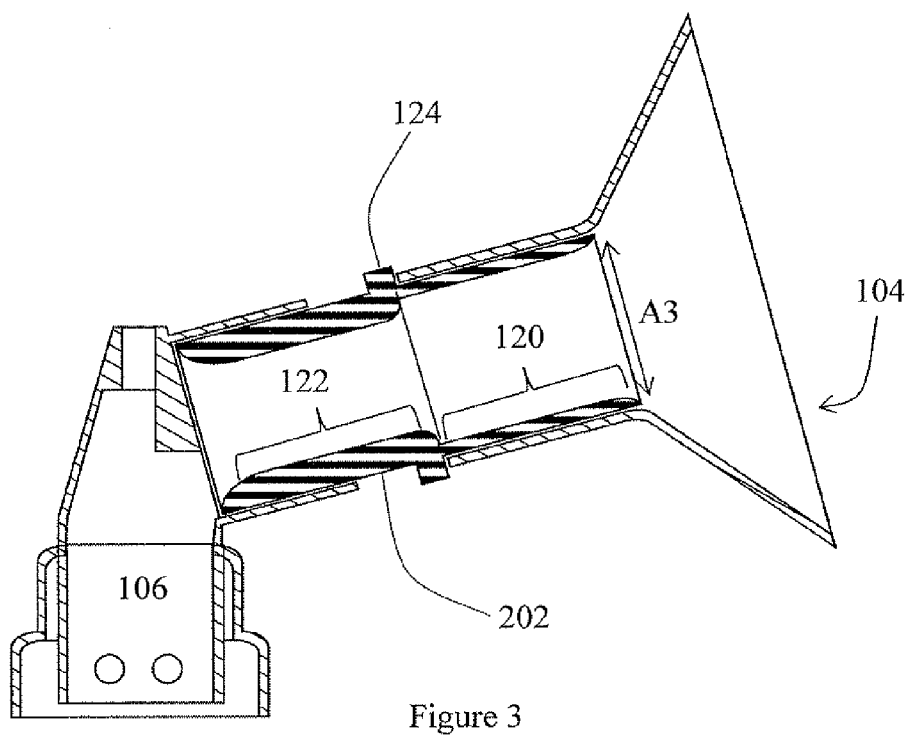
FIG. 3 is a cross-sectional view of a breast interface assembly including a dual-wall-thickness reversible element, showing the assembly in a first state.
Figure 4:
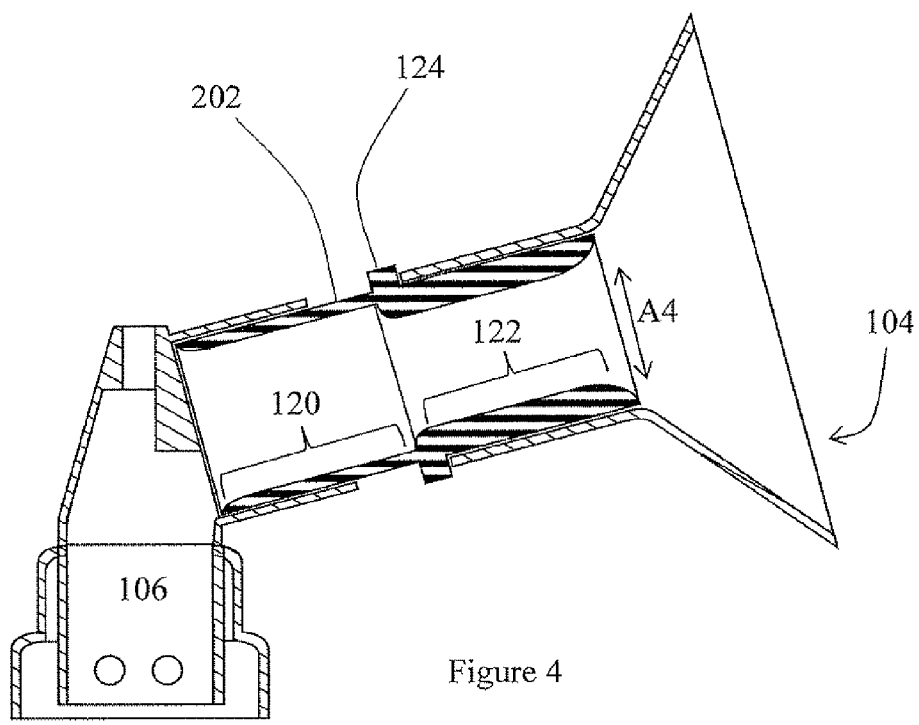
FIG. 4 is a cross-sectional view of the breast interface assembly of FIG. 3, showing the assembly in a second state.

Another embodiment is shown in FIGS. 3 and 4. FIG. 3 is a cross-sectional view of a breast interface assembly including a dual-wall-thickness reversible element, showing the element in a first configuration. The second reversible element 202 has walls of different thicknesses at its two terminal portions. In the first configuration, the second reversible element 202 is connected at a first terminal portion 120 to a breast shield 104 and, at a second terminal portion 122 to a connector 106. In the example illustrated, the nipple aperture A3 is implemented as an aperture of the second reversible element 202. To ensure a smooth transition between surfaces of the breast shield 104 and the second reversible element 202, the two ends of the second reversible element 202 have tapered edges, as outlined in FIG. 2, above. At least one abutment feature 124 serves to limit inserting the second element 202 too far into the breast shield 104. Over-insertion of the second reversible element 202 may cause discomfort and the abutment feature 124 serves to prevent over when inserted from both ends. Second reversible element 202 engages its external surfaces with internal surfaces of both the breast shield 104 and the connector 106. The first terminal portion 120 defines the nipple aperture A3.

FIG. 4 is a cross-sectional view of the breast interface assembly of FIG. 3, showing the element in a second configuration. In the second configuration, the second reversible element 202 is connected at a second terminal portion 122 to a breast shield 104 and, at a first terminal portion 120 to a connector 106. In the example illustrated, the nipple aperture A4 is implemented as an aperture of the second reversible element 202. As in FIG. 3, the two ends of the second reversible element 202 have tapered edges, as outlined in FIG. 2, above. At least one abutment feature 124 serves to limit inserting the element 202 too far into the breast shield 104. The second terminal portion 122 defines the nipple aperture A4.

The two nipple apertures produced by reversible element 102 are preferably different from the two nipple apertures produced by second reversible element 202, giving rise to four different sizes of nipple apertures. This allows provision of a modular "kit" including both of the reversible elements together with the remaining components of the breast interface assembly, thereby providing flexibility for use by mothers with a wide range of nipple sizes. Clearly, alternative kits could be formed by combining two reversible connectors of design similar to 202 but with differing wall thicknesses, or according to any of the other variant embodiments described herein.

Figure 5:
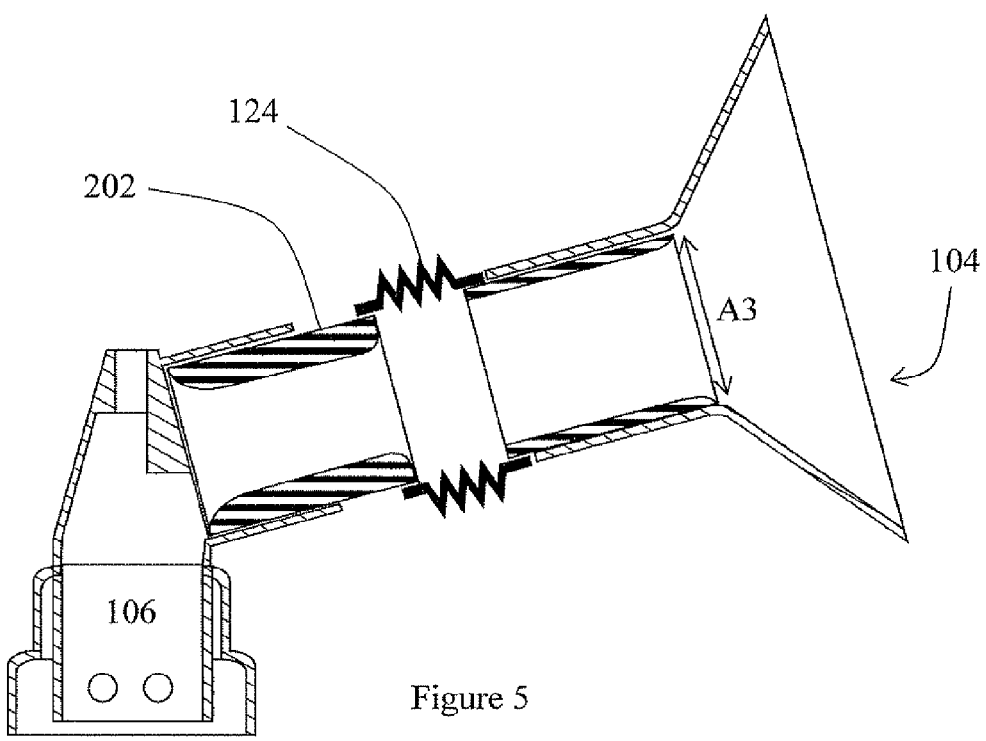
FIG. 5 is a cross-sectional view of a breast interface assembly including a flexible reversible element, showing the assembly in a first state.
Figure 6:
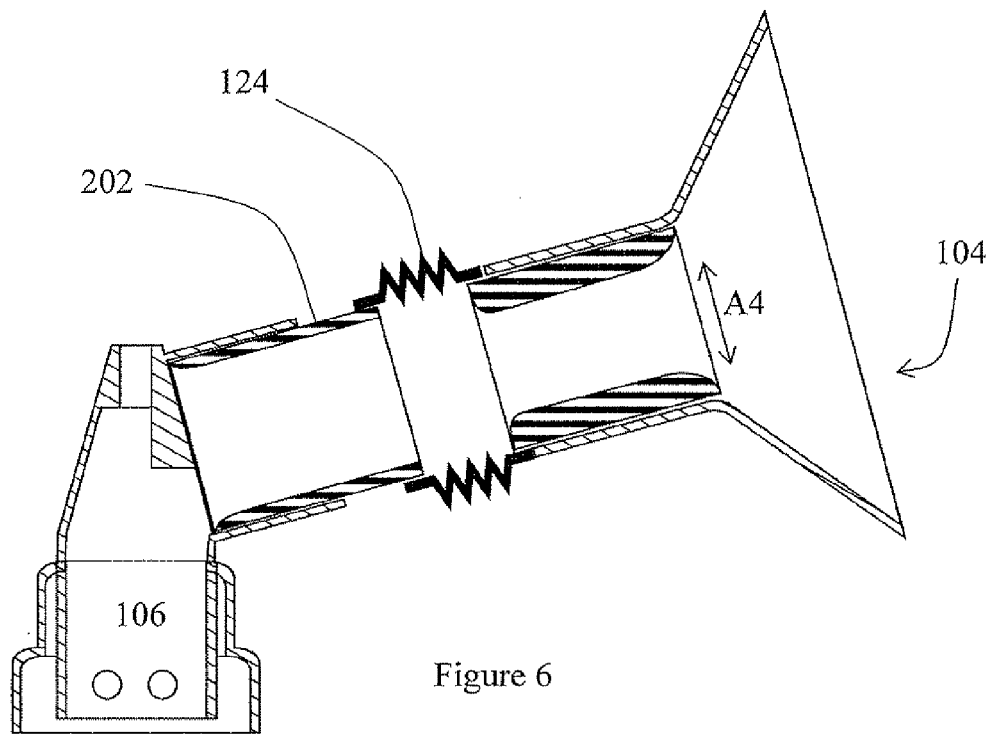
FIG. 6 is a cross-sectional view of a breast interface assembly including a flexible reversible element, showing the assembly in a second state.

Another embodiment is shown in FIGS. 5 and 6. FIGS. 5 and 6 are a cross-sectional view of a breast interface assembly, including a flexible reversible element, showing the element in a first configuration and a second configuration, respectively. A flexible section 124 may be connected to a central portion of the second reversible element 202. The flexible section 124 may be a separate component composed of a length of flexible tubing. Alternatively, the flexible section 124 may be integrally formed as part of a second reversible element 202. The flexible section 124 allows a degree of flexibility between the breast shield 104 and the connector 106, which is important for the nursing mother who may wish to adjust the angle at which the connector is held. In FIGS. 5 and 6, the flexible section 124 is shown together with a dual-wall-thickness reversible element 202. The flexible section 124 may be incorporated into any type of element, including, but not limited to, the elements described herein.

Figure 7:
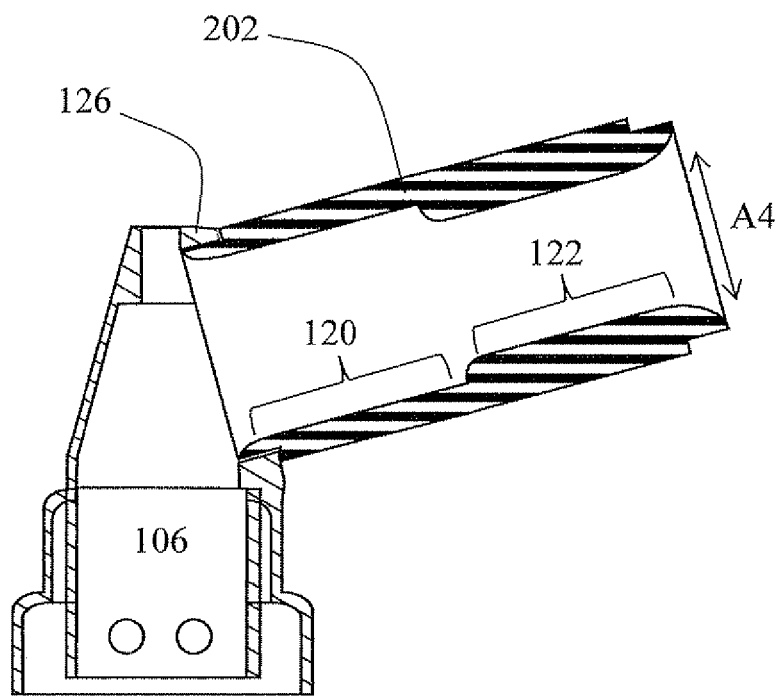
FIG. 7 is a cross-sectional view of a breast interface assembly including a dual-wall-thickness reversible element, without a flange, showing the assembly in a first state.
Figure 8:
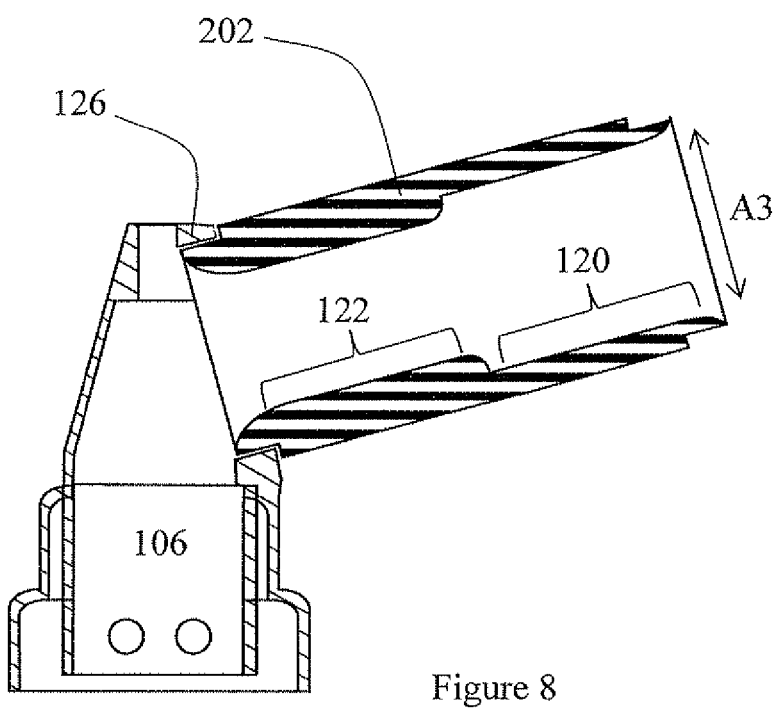
FIG. 8 is a cross-sectional view of the breast interface assembly of FIG. 7, showing the assembly in a second state.

A further embodiment is shown in FIGS. 7 and 8. FIGS. 7 and 8 are a cross-sectional view of a breast interface assembly, including a dual-wall-thickness reversible element. The breast shield 104 is absent from FIGS. 7 and 8. In this embodiment, the second reversible element 202 fits directly onto a nipple. When the second reversible element 202 is connected in a first configuration, a nipple aperture has a first diameter A3. When the second reversible element 202 is connected in a second configuration, the nipple aperture has a second diameter A4.

To securely connect the second reversible element 202, a regular press-fit seal may not hold the assembly well enough. In one embodiment, a screw thread 126 may be cut into the connector 106, and a matching thread onto an outer surface of the two ends of the second reversible element 202. Alternatively, a bayonet fitting may be employed.

The current embodiment may also encompass the flexible section described in FIGS. 5 and 6.

The breast shield adaptor may be made out of a plastic, such as polypropylene, another plastic such as polycarbonate, or a surgical rubber, such as silicone having a high durometer value. A breast interface assembly includes one breast shield 104, one connector 106, and two different reversible elements 102 and 202, one being a dual-diameter reversible element, and one being a dual-wall-thickness reversible element, providing four different sizes of nipple aperture.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A breast interface assembly for connecting a breast pump to a nipple of a breast, the breast interface assembly comprising:
   a milk inlet port; and
   a reversible element having two terminal portions of differing internal diameters, said two terminal portions being at opposing ends of said reversible element,
   wherein the breast interface assembly is configured to be assembled in a first state in which a first terminal portion of said reversible element connects with said milk inlet port and the breast interface assembly presents a breast contact surface defining a nipple aperture of a first diameter,
   and wherein the breast interface assembly is further configured to be assembled in a second state in which a second terminal portion of said reversible element connects with said milk inlet port and the breast interface assembly presents a breast contact surface defining a nipple aperture of a second diameter,
   wherein, in at least one of said first and second states, said reversible element provides at least part of said breast contact surface.

2. The breast interface assembly of claim 1, wherein said milk inlet port is part of a connector further comprising a suction port and a connection arrangement for mating with a milk receptacle.

3. The breast interface assembly of claim 1, further comprising a breast shield comprising a flange portion, said breast shield being configured to connect with said second terminal portion of said reversible element in said first state and with said first terminal portion of said reversible element in said second state, said breast shield providing at least part of said breast contact surface in each of said first and second states.

4. The breast interface assembly of claim 3, wherein said breast shield further comprises a tubular portion, said reversible element being configured such that:
   a. said second terminal portion connects internally to said tubular portion such that an internal diameter of said second terminal portion defines said nipple aperture of said first diameter; and
   b. said first terminal portion connects externally to said tubular portion such that said tubular portion defines said nipple aperture of said second diameter.

5. The breast interface assembly of claim 4, further comprising a second reversible element having two terminal portions with third and fourth internal diameters that differ from said first and second nipple aperture diameters, said second reversible element being configured for interconnecting between said milk inlet port and said breast shield in each of two configurations with said terminal portions connecting internally to said tubular portion such that internal diameters of said terminal portions define nipple apertures with said third and fourth diameters.

6. The breast interface assembly of claim 3, wherein said breast shield further comprises a tubular portion, said reversible element being configured such that both said first and second terminal portions connect internally to said tubular portion such that internal diameters of said terminal portions define said nipple aperture of said first and second diameters.

7. The breast interface assembly of claim 6, wherein said reversible element has at least one abutment feature deployed to prevent over-insertion of said reversible element into said tubular portion of said breast shield.

8. The breast interface assembly of claim 3, wherein edges of said reversible element that provide said breast contact surface are rounded so as to merge with a skin contact surface of said flange portion.

9. The breast interface assembly of claim 1, wherein said reversible element includes a flexible section to accommodate flexing of said reversible element between said first and second terminal portions.

10. The breast interface assembly of claim 1, wherein each of said first and second terminal portions of said reversible element is configured for direct sealing contact with the nipple without requiring an outwardly extending flange.

\* \* \* \* \*

UNITED STATES PATENT AND TRADEMARK OFFICE
CERTIFICATE OF CORRECTION

PATENT NO. : 8,579,874 B1  
APPLICATION NO. : 13/596071  
DATED : November 12, 2013  
INVENTOR(S) : Doron Barack Page 1 of 1

It is certified that error appears in the above-identified patent and that said Letters Patent is hereby corrected as shown below:

On the Title Page:

Item (73) the Assignee should be corrected as follows:

change
"Portable Technologies Ltd., Raanana (IL)"

to
"Clinicare Ltd., Hasadna 11, P.O.B. 701, Raanana 43106 (IL)"

Signed and Sealed this
Sixteenth Day of December, 2014

Michelle K. Lee
*Deputy Director of the United States Patent and Trademark Office*